US00PP30853P2

(12) United States Plant Patent
Ruter

(10) Patent No.: US PP30,853 P2
(45) Date of Patent: Aug. 27, 2019

(54) ***HIBISCUS* PLANT NAMED 'RUTHIB2'**

(50) Latin Name: *Hibiscus moscheutos*
Varietal Denomination: RutHib2

(71) Applicant: University of Georgia Research Foundation, Inc., Athens, GA (US)

(72) Inventor: John M. Ruter, Bishop, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/932,407

(22) Filed: Feb. 26, 2018

(51) Int. Cl.
*A01H 5/00* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — Klarquist Sparkman, LLP

(57) ABSTRACT

A new *Hibiscus* plant named 'RutHib2' is characterized by a combination of good form, medium vigor, purple foliage, magenta flowers with a red eye, and good tolerance to *Alternaria, Cercospora*, and *Phytophthora* pathogens.

1 Drawing Sheet

Genus and species: *Hibiscus moscheutos.*

Variety denomination: The new *Hibiscus moscheutos* claimed is of the cultivar denominated 'RutHib2'.

BACKGROUND OF THE INVENTION

The present invention relates to a new and distinct cultivar *Hibiscus moscheutos*, botanically known as *Hibiscus moscheutos* 'RutHib2'.

The new *Hibiscus moscheutos* 'RutHib2' is a product of a planned breeding program conducted by the Inventor Watkinsville, Ga. The objective of the *Hibiscus* breeding program is to create new plant cultivars with ornamental leaf distinctions, abundant flowers, and tolerance to pathogens.

The new *Hibiscus moscheutos* 'RutHib2' is a product of *Hibiscus moscheutos* 'Crown Jewels' (U.S. Plant Pat. No. 11,857) x '13-19' (Inventor controlled cross, not patented). 'Crown Jewels' is the female parent. The cross was made in 2011. 'RutHib2' has been evaluated through in Watkinsville, Ga. from 2012 and the plant 'RutHib2' was selected in 2013.

Asexual reproduction of the new *Hibiscus moscheutos* 'RutHib2' was by vegetative terminal cuttings in a controlled environment in Watkinsville, Ga. since 2013. These observations have shown that the unique features of this new *Hibiscus moscheutos* 'RutHib2' are stable and have reproduced true to type in successive generations.

SUMMARY OF THE INVENTION

The cultivar 'RutHib2' has not been observed under all possible environmental conditions. The phenotype may vary somewhat with variations in environment and cultural practices such as temperature and light intensity without, however, any variance in genotype.

The following represents the distinguishing characteristics of the new *Hibiscus moscheutos* cultivar named 'RutHib2'. In combination, these traits set 'RutHib2' apart from all other existing varieties of *Hibiscus* known to the inventor.

1. Good Form.
2. Medium vigor.
3. Purple foliage.
4. Magenta Flowers.
5. Good tolerance to *Alternaria, Cercospora*, and *Phytophthora* pathogens.

COMPARISON OF PARENT PLANTS

'Crown Jewels' has a height to width ratio of about 1 to 1 and is rarely more than two and one-half feet tall. 'RutHib2' can reach a height of four feet and a width of five feet eight inches. *Hibiscus* '13-19' is more rounded in shape, for example, fifty-two inches by fifty seven inches and the growth of '13-19' is more open than 'RutHib2'. Peak bloom color outside the eye zone of 'RutHib2' is RHS 67A in comparison to RHS 58A for '13-19'. 'RutHib2' flowers are also wider than '13-19' flowers.

BRIEF DESCRIPTION OF THE FIGURES

The accompanying colored photographic illustrations show the overall appearance and distinct characteristics of the new cultivar of *Hibiscus moscheutos* 'RutHib2'. The colors in the photographs are as close as possible with the photographic and printing technology utilized.

The photograph labeled FIG. 1 depicts a five year old 'RutHib2' plant.

DETAILED BOTANICAL DESCRIPTION

The following is a detailed description of the *Hibiscus moscheutos* cultivar named 'RutHib2'. Data was collected at a farm in Watkinsville, Ga. from five year old plants grown outdoors and planted in the ground.

Throughout this specification, color names beginning with a small letter signify that the name of that color, as used in common speech, is aptly descriptive. Color names beginning with a capital letter designate values based upon The R.H.S. Colour Chart, 5th edition published by The Royal Horticultural Society (R.H.S.), London, England.

Habit: Upright.

Size of plant:

A. *Height*.—114.30 cm.

B. *Width*.—173.99 cm.

Rooting: The new plant typically initiates rooting in fourteen to twenty-one days under favorable conditions.

Stem:

A. *Color*.—Greyed-purple 184-B.

B. *Length*.—115.15 cm.

C. *Diameter*.—3 cm-3.5 cm (base) 1.5 cm-1.8 cm (mid stem).

D. *Pubescence*.—None.

E. *Shape*.—Oval to Round.

F. *Odor* (*of bruised stem*).—Grassy.

G. *Internode length*.—1.8 cm-5.2 cm.

H. *Average number of stems/branches*.—50-70.

Leaf:

A. *Color* (*R.H.S.*).—1. Upper: Greyed purple 187-A to a brown purple somewhat like 200-A. 2. Lower: Green 147-B.

B. *Mature size* (*l*×*w*).—19.57 cm×13.83 cm.

C. *Apex*.—Acuminate.

D. *Base*.—Cordate.

E. *Margin*.—Erose.

F. *Shape*.—Falcate.

G. *Lobes*.—Three lobes, lobing is shallow.

H. *Pubescence*.—None.

I. *Arrangement on stem*.—Alternate.

J. *Venation*.—Reticulate.

K. *Texture*.—Glabrous (both surfaces of leaf).

Petiole:

A. *Length*.—6.5 cm-8.5 cm.

B. *Shape*.—Oval.

C. *Color* (*R.H.S.*).—Greyed orange 175-A.

D. *Pubescence*.—None.

E. *Diameter*.—0.2 cm-0.4 cm.

Flower:

A. *Inflorescence*.—1. Flowers per stem: 62-73.

B. *Individual flower*.—1. Axillary, terminal: Axillary; terminal clusters. 2. Symmetry: Actinomorphic. 3. Diameter: 14 cm. 4. Petals. a. Size (L×W) 10.5 cm×14 cm. b. Shape Obdeltoid. c. Apex Rounded. d. Base Orbicular. e. Margin Entire. f. Color at peak of bloom. i. Upper petal surface Red purple 67-A (Veins the same). ii. Lower petal surface Red purple 67-A. iii. Eye-zone Red purple 53-A. g. Number of petals 5. 5. h. Flowers are single Pedicels. a. Color (R.H.S.) Green 143-C. b. Pubescence None. c. Length 2 cm-8 cm. 6. Sepals. a. Number 5. b. Size (L×W) 4.33 cm×2.77 cm. c. Shape Ovate lanceolate. d. Pubescence Sparsely lanuginous. e. Color (R.H.S.) Yellow-green 144-A. f. Texture Both surfaces sparsely pubescent, which provides texture. 7. Stamens. a. Number 177. b. Size (L×W) 0.6 cm×<0.1 cm. c. Color (R.H.S.) Red purple N66-A. d. Pollen Color Yellow-orange 14-D. e. Pubescence None. 8. Pistils. a. Number 1 pistil with 5 stigmas. b. Size (L×W) 4.7 cm×0.4-0.9 cm. c. Color of Style (R.H.S.) Red purple 63-C. d. Color of Stigma (R.H.S.) Red purple 63-A. 9. Bracts. a. Number 12 b. Size 2.9 cm (L). c. Color (R.H.S.) Green 143-A.

C. *Fruit*.—Fruit typical of species.

D. *Seed*.—Number of seed per fruit is variable, seed 4 mm wide by 4 mm long, oval to round in shape, color Brown 200 D.

E. *Bloom time*.—In Watkinsville, Ga., plants typically begin blooming in late May and continue blooming through mid-July.

F. *Fragrance*.—No apparent fragrance.

Winter hardiness: The plant has been observed in Watkinsville, Ga., U.S. hardiness zone 8a; and in West Grove, Pa., U.S. hardiness zone 6b.

What is claimed is:

1. A new and distinct cultivar of the *Hibiscus* plant named 'RutHib2' as illustrated and described herein.

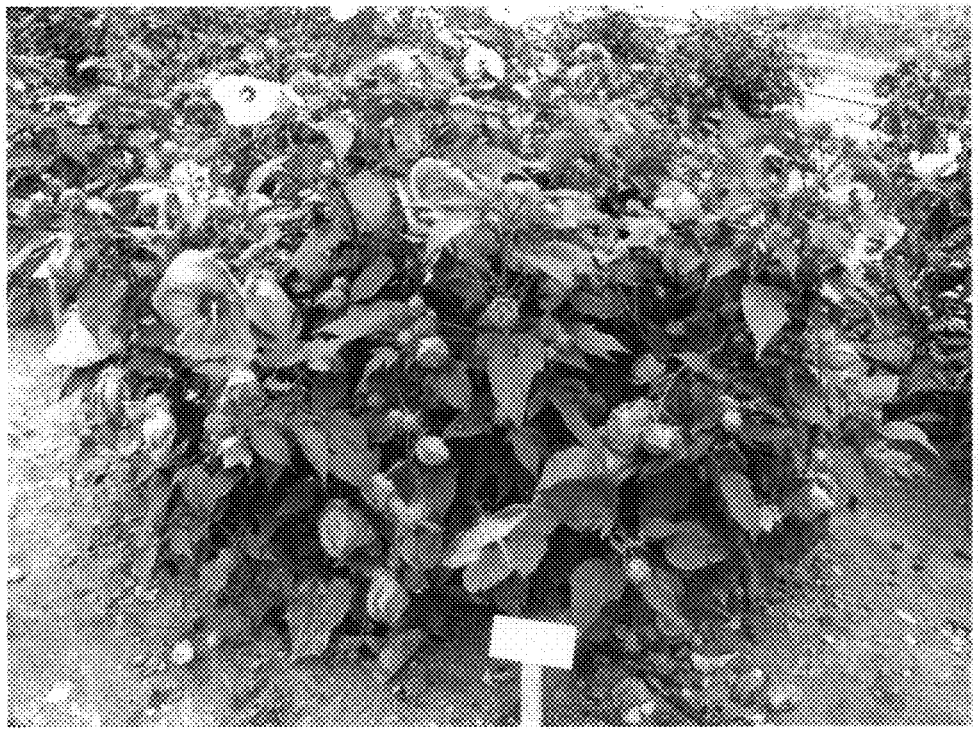

* * * * *